United States Patent
Ting

(10) Patent No.: US 10,918,268 B2
(45) Date of Patent: Feb. 16, 2021

(54) INSERT TUBE AND ENDOSCOPE USING THE SAME

(71) Applicant: OPCOM INC., New Taipei (TW)

(72) Inventor: Chih-Yu Ting, New Taipei (TW)

(73) Assignee: OPCOM INC., New Taipei (TW)

(*) Notice: Subject to any disclaimer, the term of this patent is extended or adjusted under 35 U.S.C. 154(b) by 388 days.

(21) Appl. No.: 15/856,077

(22) Filed: Dec. 28, 2017

(65) Prior Publication Data

US 2019/0059699 A1    Feb. 28, 2019

Related U.S. Application Data

(60) Provisional application No. 62/551,264, filed on Aug. 29, 2017.

(51) Int. Cl.
*A61M 25/00* (2006.01)
*A61B 1/005* (2006.01)
*A61B 1/04* (2006.01)
*A61B 1/05* (2006.01)

(52) U.S. Cl.
CPC .......... *A61B 1/0056* (2013.01); *A61B 1/0052* (2013.01); *A61B 1/0055* (2013.01); *A61B 1/04* (2013.01); *A61B 1/05* (2013.01); *A61M 25/0054* (2013.01)

(58) Field of Classification Search
CPC combination set(s) only.
See application file for complete search history.

(56) References Cited

U.S. PATENT DOCUMENTS

| 5,885,288 A * | 3/1999 | Aust ...................... A61B 17/29 604/22 |
| 8,979,739 B2 * | 3/2015 | Seto .................. A61M 25/0138 600/139 |
| 10,507,107 B2 * | 12/2019 | Nathe ..................... A61F 2/246 |
| 2003/0125711 A1 * | 7/2003 | Eidenschink ..... A61M 25/0108 604/529 |
| 2005/0177131 A1 * | 8/2005 | Lentz ................. A61M 25/0013 604/525 |
| 2005/0272976 A1 * | 12/2005 | Tanaka ............... A61B 1/00073 600/114 |
| 2005/0288656 A1 * | 12/2005 | Koerner ................. A61B 18/02 606/21 |
| 2007/0100285 A1 * | 5/2007 | Griffin .............. A61M 25/0013 604/164.11 |

(Continued)

*Primary Examiner* — Anh Tuan T Nguyen
*Assistant Examiner* — Shankar Raj Ghimire
(74) *Attorney, Agent, or Firm* — Amin, Turocy & Watson, LLP

(57) ABSTRACT

An insert tube and an endoscope using the same are provided. The insert tube comprises a catheter. The catheter comprises a distal section, a bending section and a extend section, and the distal section. The bending section and the extend section are integrally formed through a metal material. A plurality of a first line groove and a plurality of second line groove are formed and arranged in staggered relation on two corresponding sides of the bending section along the central axis direction of the catheter, respectively. At least one the second line groove is arranged between the first line grooves. The first line groove and the second line groove have a first arc length and a second arc length, respectively. A length of the first arc length is greater than a length of the second arc length.

12 Claims, 5 Drawing Sheets

(56) References Cited

U.S. PATENT DOCUMENTS

| | | | |
|---|---|---|---|
| 2008/0097395 A1* | 4/2008 | Adams | A61M 25/0021 604/524 |
| 2008/0125753 A1* | 5/2008 | Chen | A61M 25/0013 604/528 |
| 2008/0249436 A1* | 10/2008 | Darr | A61B 10/0275 600/585 |
| 2009/0137875 A1* | 5/2009 | Kitagawa | A61B 1/0052 600/146 |
| 2009/0177119 A1* | 7/2009 | Heidner | A61M 25/09 600/585 |
| 2010/0063479 A1* | 3/2010 | Merdan | A61B 1/0011 604/528 |
| 2011/0034772 A1* | 2/2011 | Konstorum | A61B 1/00071 600/142 |
| 2011/0230718 A1* | 9/2011 | Akui | A61B 1/0052 600/146 |
| 2011/0251519 A1* | 10/2011 | Romoscanu | A61M 25/0013 600/585 |
| 2011/0276034 A1* | 11/2011 | Tomarelli | A61M 25/0054 604/528 |
| 2012/0029281 A1* | 2/2012 | Frassica | A61B 1/00082 600/114 |
| 2012/0245418 A1* | 9/2012 | Boulais | A61B 1/00103 600/142 |
| 2012/0277730 A1* | 11/2012 | Salahieh | A61B 1/00135 604/527 |
| 2013/0096553 A1* | 4/2013 | Hill | A61N 1/05 606/41 |
| 2014/0163321 A1* | 6/2014 | Seto | A61M 25/0138 600/139 |
| 2014/0296636 A1* | 10/2014 | Hatano | A61B 1/0008 600/112 |
| 2016/0345947 A1* | 12/2016 | Salahieh | A61M 25/0138 |
| 2017/0000977 A1* | 1/2017 | Storbeck | A61M 25/0013 |
| 2017/0027421 A1* | 2/2017 | Imai | A61B 1/00091 |
| 2017/0080186 A1* | 3/2017 | Salahieh | A61M 25/0053 |
| 2017/0224192 A1* | 8/2017 | Seto | A61B 1/00 |
| 2017/0319317 A1* | 11/2017 | Biscay | A61D 19/027 |
| 2018/0042451 A1* | 2/2018 | Cuscuna | A61B 1/0011 |
| 2018/0093070 A1* | 4/2018 | Cottone | A61M 25/0021 |
| 2018/0304040 A1* | 10/2018 | Jalgaonkar | A61M 25/0054 |
| 2019/0008640 A1* | 1/2019 | Cooper | A61F 2/2439 |
| 2019/0110788 A1* | 4/2019 | Lombardo | A61B 17/0469 |
| 2019/0117193 A1* | 4/2019 | Cuscuna | A61B 8/12 |
| 2019/0269491 A1* | 9/2019 | Jalgaonkar | A61B 17/221 |
| 2020/0253731 A1* | 8/2020 | Manash | A61F 2/2439 |

* cited by examiner

INSERT TUBE AND ENDOSCOPE USING THE SAME

CROSS REFERENCE TO RELATED APPLICATIONS

This application claims the benefit of U.S. Provisional Application No. 62/551,264, which was filed on Aug. 29, 2017 and is incorporated herein by reference.

BACKGROUND OF THE INVENTION

1. Field of the Invention

The invention relates in general to an insert tube and an endoscope using the same, and more particularly to a catheter of an insert tube integrally formed through a metal material and an endoscope using the same.

2. Description of the Prior Art

The endoscope includes a distal end, a bending section, a tube and a handle. An end of the bending section connects to an end of the tube to form an insert tube. The distal end connects to the other end of the bending section, and the other end of the tube connects to the handle. The handle controls the bending section to bend any angles as needed.

If the end of the bending section which has diameter A can be inserted into the end of the tube which has diameter B, the insert tube can be assembled. The diameter B may be greater than the diameter A. However, in a case of the endoscope having the bending section at the insert tube, when various components disposed in the insert tube is increase, the diameter A and the diameter B may be increase and the cost of the endoscope may be increase, it becomes difficult to connect the bending section and the tube, and the connection relationship between the bending section and the tube may be reduced, and the endoscope may not be waterproof and reusable.

Therefore, it is in need to provide novel insert tube, insert tube of an endoscope integrally formed in one piece and having wide radii of curvature of the insert tube.

SUMMARY OF THE INVENTION

The disclosure is directed to an insert tube and an endoscope using the same. The insert tube is integrally formed in one piece and having wide radii of curvature of the insert tube.

According to one aspect of the present disclosure, an insert tube is provided. The insert tube comprises a catheter. The catheter comprises a distal section, a bending section and a extend section, and the distal section. The bending section and the extend section are integrally formed through a metal material. A plurality of a first line groove and a plurality of second line groove are formed and arranged in staggered relation on two corresponding sides of the bending section along the central axis direction of the catheter, respectively. At least one the second line groove is arranged between the first line grooves. The first line groove and the second line groove have a first arc length and a second arc length, respectively. A length of the first arc length is greater than a length of the second arc length.

According to another aspect of the present disclosure, an endoscope is provided. The endoscope comprises an insert tube. The insert tube comprises a catheter. The catheter comprises a distal section, a bending section and a extend section, and the distal section. The bending section and the extend section are integrally formed through a metal material. A plurality of a first line groove and a plurality of second line groove are formed and arranged in staggered relation on two corresponding sides of the bending section along the central axis direction of the catheter, respectively. At least one the second line groove is arranged between the first line grooves. The first line groove and the second line groove have a first arc length and a second arc length, respectively. A length of the first arc length is greater than a length of the second arc length.

According to another aspect of the present disclosure, an endoscope is provided. The endoscope comprises a camera module, a handle and an insert tube. The insert tube comprises a catheter. The catheter comprises a distal section, a bending section and a extend section, and the distal section. The bending section and the extend section are integrally formed through a metal material. A plurality of a first line groove and a plurality of second line groove are formed and arranged in staggered relation on two corresponding sides of the bending section along the central axis direction of the catheter, respectively. At least one the second line groove is arranged between the first line grooves. The first line groove and the second line groove have a first arc length and a second arc length, respectively. A length of the first arc length is greater than a length of the second arc length. An end of the handle connects to an end of the insert tube. The camera module is disposed in the distal end.

By the features described above, the present invention provides an insert tube and an endoscope using the same, the insert tube is integrally formed through a metal material, and the bending section is elastic and bent at any angle as needed in accordance with the arrangement relationship of the first line grooves and the second line grooves, the shape of the first line grooves and the shape of the second line grooves for increasing the curvature and the extensibility of the bending section.

The above and other aspects of the disclosure will become better understood with regard to the following detailed description of the non-limiting embodiment(s). The following description is made with reference to the accompanying drawings.

These and other objectives of the present invention will no doubt become obvious to those of ordinary skill in the art after reading the following detailed description of the preferred embodiment that is illustrated in the various figures and drawings.

DETAILED DESCRIPTION

Preferred embodiments are disclosed below for elaborating the invention. Various lengths, such as optical focus lengths or distances, of a plurality of micro lenses are applied on a plurality of detecting pixels, such that in an autofocus process, the time consumption can be reduced, and the accuracy can be improved. The following embodiments are for the purpose of elaboration only, not for limiting the scope of protection of the invention. Besides, secondary elements are omitted in the following embodiments to highlight the technical features of the invention.

Figure 1:
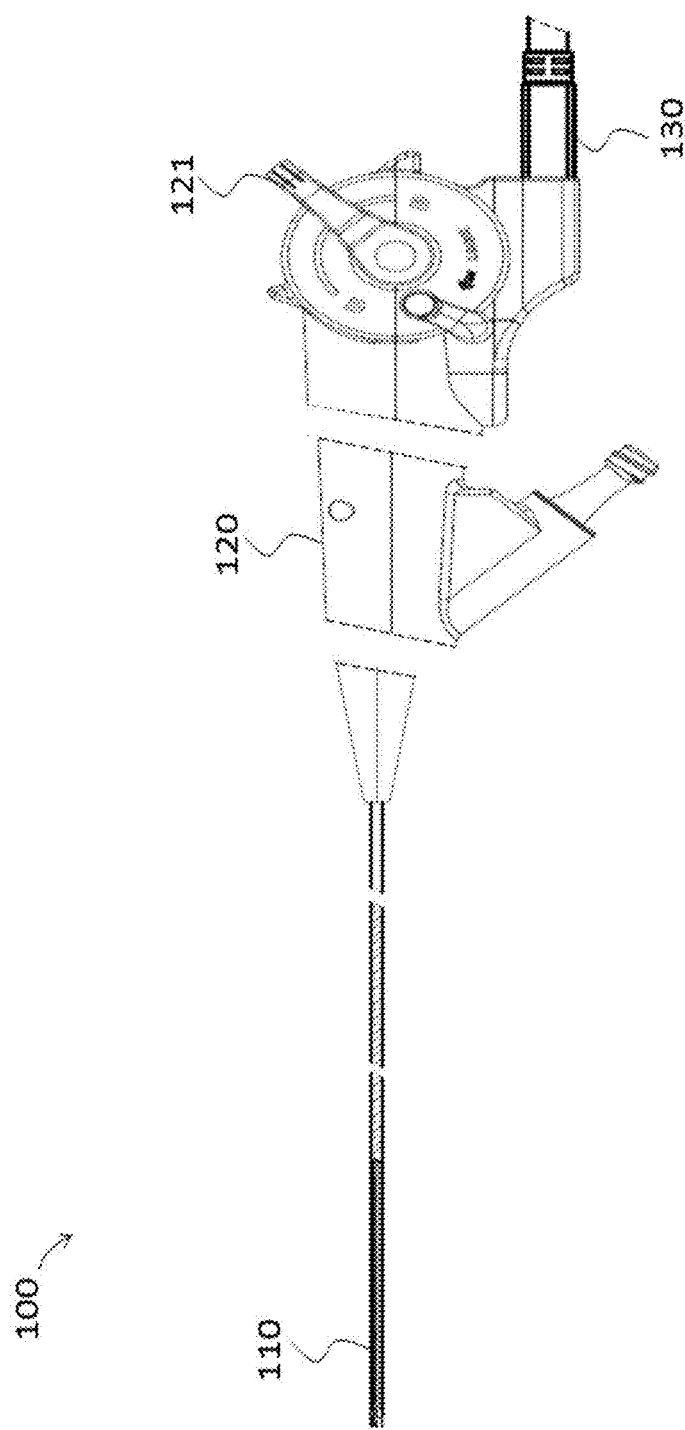
FIG. 1 is a side view schematically showing a whole endoscope according to one embodiment of the present invention.

Reference is now made to FIG. 1, which is a side view schematically showing a whole endoscope according to one embodiment of the present invention. As shown in FIG. 1, the endoscope 100 includes an insert tube 110, a handle 120 and a cable 130. Wherein, an end of the handle 120 connects to an end of the insert tube 110, and the other end of the handle 120 connects to an end of the cable 130. The endoscope 100 may be a disposable endoscope or a reusable endoscope. The disposable endoscope or the reusable endoscope may be chosen in accordance with user's needed. The insert tube 110 may be a flexible tube or an inflexible tube. But it is not limit this invention.

Figure 2A:
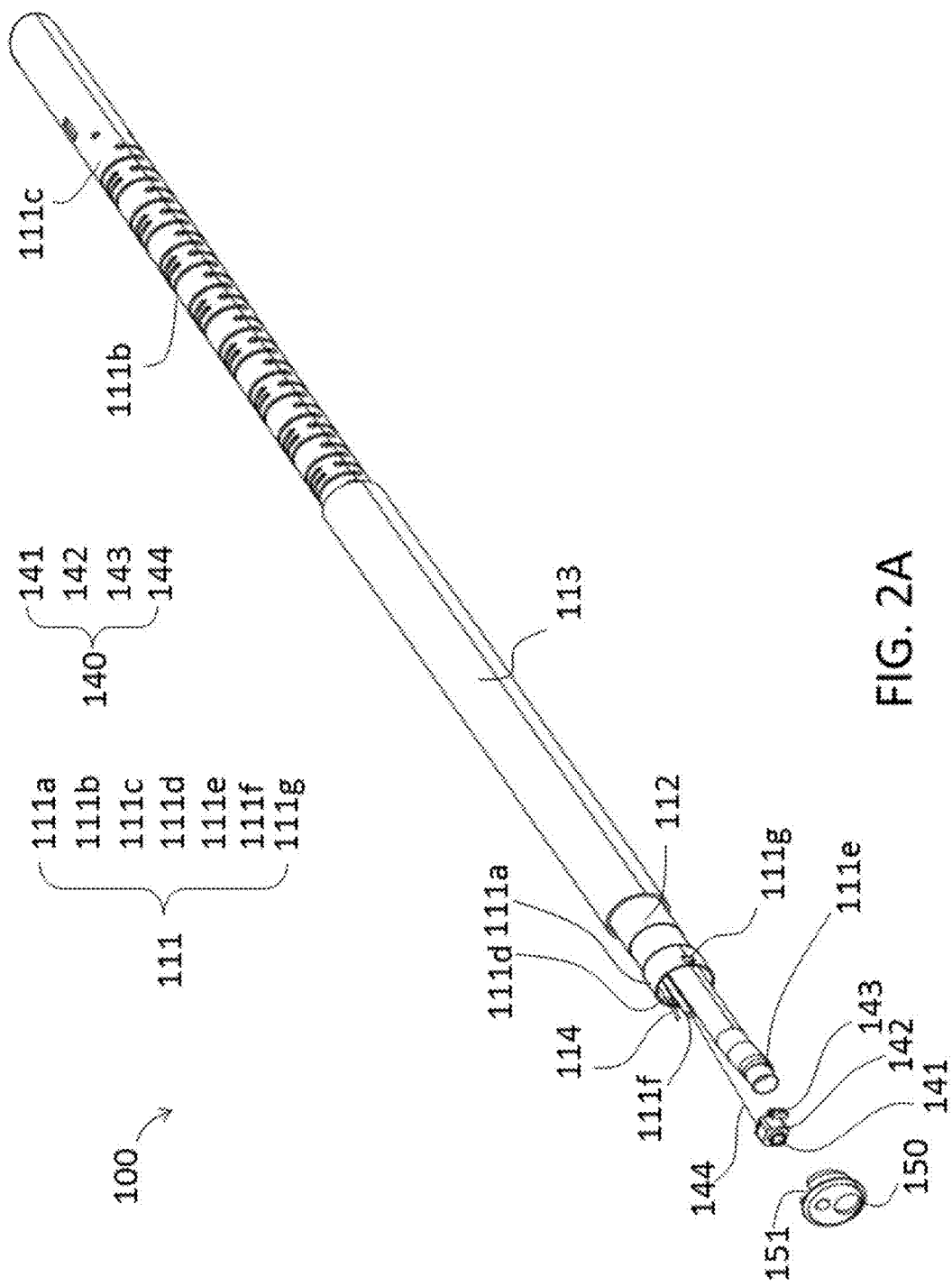
FIG. 2A is a perspective view of an insert tube of the endoscope of FIG. 1.
Figure 2B:
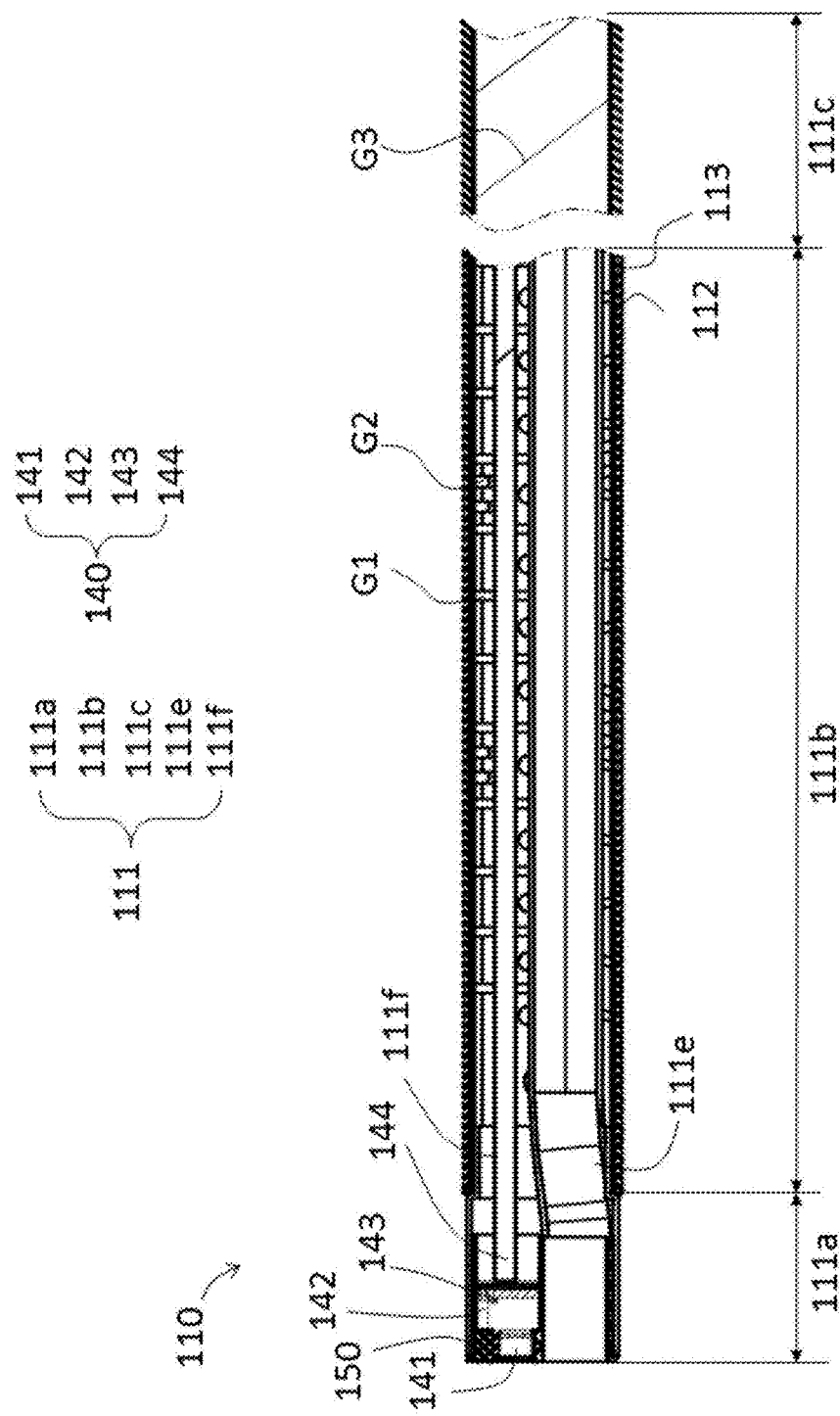
FIG. 2B is a longitudinal section view of the insert tube of the endoscope of FIG. 1.
Figure 2C:
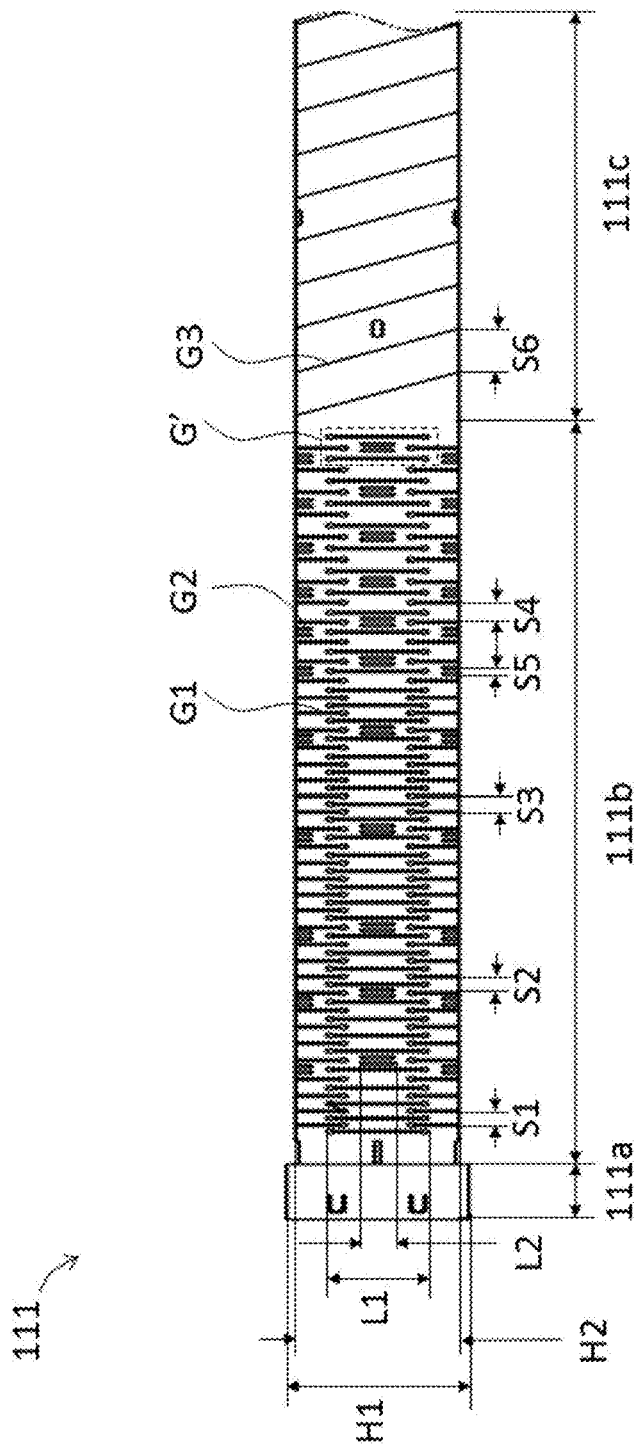
FIG. 2C is a plan view of an expanding catheter of the insert tube of FIG. 2A.

Please refer to FIG. 2A, which is a perspective view of an insert tube of the endoscope of FIG. 1. Please refer to FIG. 2B, which is a longitudinal section view of the insert tube of the endoscope of FIG. 1. Please refer to FIG. 2C, which is a sectional view of a catheter of the insert tube of FIG. 2A. As shown in FIG. 1 to FIG. 2C, the insert tube 110 includes a catheter 111, a first cladding unit 112 and a second cladding unit 113. The first cladding unit 112 into which the catheter 111 is inserted, the second cladding unit 113 into which the first cladding unit 112 is inserted. In other words, the first cladding unit 112 may be configured to cover the outer face of the catheter 111, and the second cladding unit 113 may be configured to cover the outer face of the first cladding unit 112 tightly.

The catheter 111 includes a distal section 111a, a bending section 111b and a extend section 111c. The distal section 111a, the bending section 111b and the extend section 111c may be connected and arranged from top to bottom of the catheter 111. Moreover, the distal section 111a, the bending section 111b and the extend section 111c are integrally formed through a metal material. In other words, the catheter 111 may be differentiated or divided into the distal section 111a, the bending section 111b and the extend section 111c. An end of the extend section 111c connects to the end of the handle 120. Therefore, an end of the distal section 111a and the end of the extend section 111c may be defined as two ends of the catheter 111, respectively. The distal section 111a has a first diameter H1 and the bending section 111b has a second diameter H2, a length of the first diameter H1 is greater than the length of a second diameter H2. The catheter 111 may be a stainless steel tube, or an elastic waterproof tube made from rigid material which may be bent at any angle, but it is not limit this invention.

In one embodiment, the first cladding unit 112 may be configured to cover from the outer surface of the bending section 111b to the outer surface of the extend section 111c of the catheter 111, and the second cladding unit 113 may be configured to cover the first cladding unit 112. For example, the outside of the insert tube 110 may be equal to or smaller than 3.5 millimeter.

A plurality of a first line groove G1 and a plurality of second line groove G2 are formed and arranged on the bending section 111b. The first line grooves G1 and the second line grooves G2 may be formed and arranged in staggered relation on two corresponding sides of the bending section 111b along the central axis direction of the catheter 111, respectively. In the other words, the first line grooves G1 may be arranged in staggered relation on two corresponding sides of the bending section 111b along the central axis direction of the catheter 111, and the second line grooves G2 may be arranged in staggered relation on two corresponding sides of the bending section 111b along the central axis direction of the catheter 111. Furthermore, the first line grooves G1 and the second line grooves G2 may be arranged between the distal section 111a and the extend section 111c. The central axis direction of the catheter 111 and a central axis of the catheter 111 may be parallel. In the other words, the central axis direction of the catheter 111 may be determined from the end of distal section 111a to the end of the extend section 111c or the other end of the insert tube 110 to the end of the handle 120. In one embodiment, at least one the second line groove G2 may be arranged between the first line grooves G1. The first line grooves G1 may be arranged parallel on the bending section 111b, and the second line grooves G2 may be arranged parallel on the bending section 111b. Furthermore, the first line grooves G1 and the second line grooves G2 may be arranged parallel and in staggered relation to one another on the bending section 111b along the central axis direction of the catheter 111.

In one embodiment, the first line groove G1 has a first arc length L1; the second line groove G2 has a second arc length L2. A length of the first arc length L1 may be greater than a length of the second arc length L2. The first line groove G1 and the second line groove G2 may be openings, holes or line-shaped recess. In the other words, shapes of the first line grooves G1 or the second line grooves G2 may be line-shaped, I-shaped or 1-shaped. The second line grooves G2 may be a line-shaped recess.

In one embodiment, the first line grooves G1 and the second line grooves G2 may be formed on the bending section 111b in accordance with a laser cutting, plasma cutting or water-jet cutting method. A direction of the arrangement relationship of the first line grooves G1 may be defined as the central axis direction of the catheter 111 which is perpendicular to the shape of each first line groove G1, and/or a direction of the arrangement relationship of the second line grooves G2.

In another embodiment, at least two the second line grooves G2 are arranged between the two first line grooves G1. For example, the two second line grooves G2 are arranged between the two first line grooves G1 to form the first shaped structure G'. The catheter 111 includes a plurality of the first line grooves G1 and a plurality of the first shaped structure G'. A shape of the first shaped structure G' may be H-shaped. Furthermore, the two second line grooves G2 of the first shaped structure G' are parallel, and the two second line grooves G2 and the two first line grooves G1 of the first shaped structure G' are parallel to one another. The first shaped structures G' are formed and arranged in staggered relation on two corresponding sides of the bending section 111b along the central axis direction of the catheter 111, but it is not limit this invention.

In another embodiment, a number of the first line grooves G1 are formed and arranged on the bending section 111b in increasing order to decreasing order to increasing order along the central axis of the catheter 111. A number of the second line grooves G2 are arranged on the bending section 111b in increasing order to decreasing order to increasing order along the central axis of the catheter 111, but it is not limit this invention.

In another embodiment, when a number of the first line grooves G1 are arranged on the bending section 111b in increasing order to decreasing order to increasing order along the central axis of the catheter 111, a number of the first shaped structures G' are arranged on the bending section 111b in decreasing order to increasing order along the central axis of the catheter 111. Furthermore, the first shaped structure G' is arranged between the first line grooves G1.

In one embodiment, a first distance S1 is between every two first line grooves G1. In the other words, each first line grooves G1 is arranged on the bending section 111b at the first distance S1. A second distance S5 is between every two the second line grooves G2. In another embodiment, the second distance S5 may be between the two second line grooves G2 of the first shaped structure G'. Furthermore, the two second line grooves G2 are arranged and disposed in the region of the first distance S1 of the two first line grooves G1.

In one embodiment, a plurality of different distance, for example, the first distance S1, a fourth distance S2, a fifth distance S3 and a sixth distance S4 are between any two first line grooves G1, respectively. In the other words, the first distance S1, the fourth distance S2, the fifth distance S3 and the sixth distance S4 are different. All of the different distances are increase from the bending section 111b to the extend section 111c. Therefore, the sixth distance S4 is greater than the fifth distance S3. The fifth distance S3 is greater than the fourth distance S2. The fourth distance S2 is greater than the first distance S1. Therefore, the bending section 111b of the catheter 111 of the insert tube 110 may be bent at any angle as needed in accordance with a plurality of different distances are between any two first line grooves G1, respectively.

In one embodiment, for example, the first distance S1 may be equal to the fourth distance S2. The fifth distance S3 may be equal to the sixth distance S4. The fifth distance S3 and the sixth distance S4 is greater than the first distance S1 and the fourth distance S2. Therefore, the bending section 111b of the catheter 111 of the insert tube 110 may be bent at any angle as needed in accordance with a plurality of different distances, such as the first distance S1, the fourth distance S2, the fifth distance S3 and the sixth distance S4 are between any two first line grooves G1, respectively.

The extend section 111c includes a third line groove G3. Furthermore, the third line groove G3 is formed in a spiral shape around the axis relative to the extend section 111c. In the other words, the third line groove G3 is formed on the extend section 111c along the central axis direction of the catheter 111. The third line groove G3 may be further formed from the extend section 111c to the end of the handle 120. The third line groove G3 may be formed in the spiral shape at a third distance S6. The third line groove G2 may be formed on the extend section 111c in accordance with a laser cutting, plasma cutting or water-jet cutting method.

In one embodiment, the first line grooves G1, the second line grooves G2 and the third line grooves G3 may not connect with each other, but it is not limit this invention.

Please refer to FIG. 1 to FIG. 2A, the insert tube 110 further includes a controlling unit 114. The catheter 111 includes a controlling channel (not shown). In the other words, the controlling channel may be formed in the catheter 111. The controlling channel is provided in the catheter 111, opening between the bending section 111b and the distal section 111a of the catheter 111 in the central axis direction and opening at the end of handle 120 of the endoscope 100. The controlling unit 114 further connects to the internal wall of the bending section 111b. The controlling unit 114 disposed through the controlling channel of the catheter 111, and an end of the controlling unit 114 connects between the distal section 111a and the bending section 111b, the other end of the controlling unit 114 connects to the handle 120.

The controlling unit 114 controls the bending section 111b to bend and move in accordance with the first line grooves G1 and the second line grooves G2.

For example, the controlling unit 114 may have two stainless steel lines. The two controlling channels may be formed in the catheter 111. The two stainless steel lines may be disposed through the two controlling channels, respectively. The two controlling channels may be disposed in two insides of the catheter 111, but it is not limit this invention.

In one embodiment, the catheter 111 further includes two fixed components (not shown). The handle 120 includes a space (not shown) formed in the inside of the handle 120 and a rotating unit disposed in the space (not shown). The fixed components are positioned on the internal walls of bending section 111b, and further are disposed on two corresponding insides of the bending section 111b, respectively. The end of the controlling unit 114 connects to the fixed component, and the other end of the controlling unit 114 connects to the rotating unit. The controlling unit 114 may be fixed to the inside of the bending section 111b of the catheter 111 in accordance with the fixed components. When the controlling unit 114 may be moved relatively with the handle 120, the controlling unit 114 may control the bending section 111b of the catheter 111 fixed with the fixed components to be moved or bent.

Figure 3:
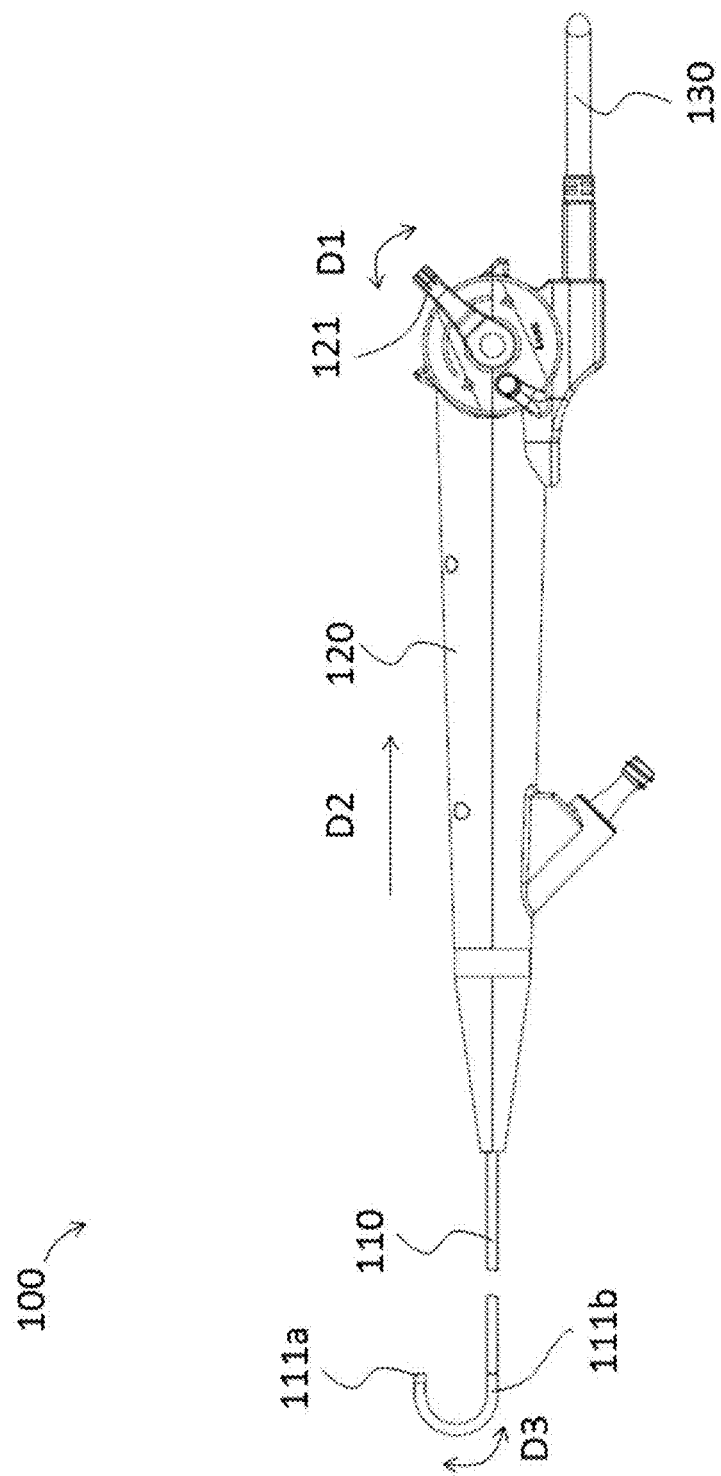
FIG. 3 is a side view schematically showing a whole endoscope, and the bending section of the insert tube of the endoscope is controlled to bend in a third direction of FIG. 1.

Please refer to FIG. 3, which is a side view schematically showing a whole endoscope, and the bending section of the insert tube of the endoscope is controlled to bend in a third direction of FIG. 1. Please refer to FIG. 1, FIG. 2A and FIG. 3, the handle 120 includes an operational unit 121. The operational unit 121 is disposed on the outside of the handle 120 and connects to the rotating unit (not shown). When the operational unit 121 may be controlled to move, the rotating unit may be rotated in accordance with the operational to move the controlling unit 114, and the controlling unit 114 connected with the fixed components may be moved to control the bending section 111b to bend at any angle. Because the first line grooves G1 and the second line grooves G2 are formed and arranged on the bending section 111b, the bending section 111b of the catheter 111 made from a metal material can be elastic. Therefore, when the controlling unit 114 may control the bending section 111b, the bending section 111b may be bent at any angle in accordance with the first line grooves G1 and the second line grooves G2. In the other words, when the operational unit 121 may be moved relatively with the handle 120, such as the operational unit 121 may move along a first direction D1, the rotating unit may rotate with the operational unit 121 to make the controlling unit 114 move along a second direction D2, and the bending section 111b may be bent in a third direction D3.

To summarize, the distal section 111a, the bending section 111b and the extend section 111c are integrally formed through a metal material and formed to the catheter ill, and the first line grooves G1 and the second line grooves G2 are formed and arranged on the bending section 111b, and the first line grooves G1 and the second line grooves G2 are arranged in staggered relation, and a number of the first line grooves G1 and a number of the second line grooves G2 are further arranged in increasing order and/or decreasing order, respectively. And the third line groove G3 is formed in a spiral shape around the axis relative to the extend section 111c from the extend section 111c to the handle 120. When the bending section 111b of the catheter 111 of the insert tube 110 may be bent with the operational unit 121, the bending section 111b may be elastic to move and bend at any angle in accordance with the first line grooves G1 and the second line grooves G2. A curvature of the bending section 111b may be adjusted and fine-tuned with the first line grooves G1 and the second line grooves G2 as needed. And the insert tube 110 may be moved with the third line groove G3.

In another embodiment, each first line groove G1 and each second line groove G2 are arranged in staggered relation with each other, and each first line groove G1 and each second line groove G2 are further arranged in staggered relation along the second direction D2 or the reverse second direction D2. A direction of the arrangement relationship of the first line grooves G1 and the second line grooves G2 may be perpendicular to the shape of each first line groove G1 and/or the shape of each second line groove G2. The direction of the arrangement relationship of the first line grooves G1 and the second line grooves G2 may be determined the central axis direction of the catheter 111. But the present invention is not limited to the embodiments explained above.

In one embodiment, the catheter 111 of the insert tube 110 includes an instrument channel 111e. In the other words, the instrument channel 111e may be formed in the catheter 111. The instrument channel 111e is provided in the catheter 111, opening at the end of the distal section 111a of the catheter 111 in the central axis direction and opening at the end of handle 120 of the endoscope 100. The controlling channel and the instrument channel 111e may be adjoined with each other. In another embodiment, two controlling channels may be disposed on two corresponding sides of the instrument channel 111e, and all of them may be adjoined to one another. The instrument channel 111e may be configured for insertion of a surgical tool (not shown) to operate on various tissues.

In one embodiment, the first cladding unit 112 substantially may be a braid which is a net-like tube, disposed so as to cover an outer of catheter 111. The first cladding unit 112 may be fixed on the catheter 111 in accordance with the arrangement relationship of the first line grooves G1 and the second line grooves G2, from the bending section 111b to the extend section 111c. The first cladding unit 112 may further cover and fix stably on the catheter 111 in accordance with a number of the first shaped structure G' arranged in increasing order and/or decreasing order on the bending section 111b. The first line grooves G1, the second line grooves G2 and the first cladding unit 112 may be provided to increase the curvature and the extensibility of the bending section 111b and the life time of the insert tube 110.

The first cladding unit 112 is, for example, a tubular net-like body formed by fibers of a metal material such as a stainless steel material, a resin material or a silicone material such as aramid fiber are braided into a net-like shape.

In one embodiment, the second cladding unit 113 substantially may be a tube, disposed so as to cover an outer of the first cladding unit. The second cladding unit 113 is made of, for example, a plastic material or a silicone material. The second cladding unit 113 may be a heat shrink tubing. When the second cladding unit 113 covers the outer of the first cladding unit, the second cladding unit 113 may be fixed on the first cladding unit 112 formed by a heating process or a processing which is provided to shrink the whole second cladding unit 113 for protecting the insert tube 110.

Please refer to FIG. 1 and FIG. 2, in one embodiment, the endoscope 100 includes a camera module 140 and a fixture 150. The camera module 140 may be disposed in the distal section 111a of the catheter 111. Furthermore, the fixture 150 may be disposed in the end of the distal section 111a and the camera module 140 may be disposed in the fixture 150. The catheter 111 of the insert tube 110 includes a camera channel 111f. In the other words, the camera channel 111f may be formed in the catheter 111. The camera channel 111f is provided in the catheter 111, opening at the end of the distal section 111a of the catheter 111 in the central axis direction and opening at the end of handle 120 of the endoscope 100.

At least two openings are formed on a surface of the fixture 150. The camera module 140 includes a camera 141, at least one light emitter unit 142, a first circuit board 143 and a first wire 144. Wherein, the first circuit board 143 electronically connects to the camera 141, light emitter units 142 and an end of the first wire 144. The camera 141 is disposed in the one of the openings of the fixture 150. The camera module 140 may have the two light emitter units 142 disposed to two corresponding sides of the camera 141. The other end of the first wire 144 electronically connects to a second circuit board of the handle 120 (not shown). The first circuit board 143 and the second circuit board may be a printed circuit board (PCB), respectively. In one embodiment, the instrument channel 111e may further be connected and opening at the other of the openings of the fixture 150. The surgical tool may be inserted from an opening of the handle 120, and disposed through the instrument channel 111e, and exposed from the other of opening of the fixture 150.

An opening (not shown) is determined formed at the end of the distal section 111a and the fixture 150 may further be posited and connected to the opening of the distal section 111a. The surface of the fixture 150 and the opening of the distal section 111a may be on a same face. In one embodiment, the surface of the fixture 150 and the opening of the distal section 111a may be on two different faces; such as a part of the fixture 150 is exposed from the end of the distal end or a distance is between the surface of the fixture 150 and the end of the distal section 111a.

The fixture 150 may be fixed to the distal section 111a byway of hook, fitting or insertion and the distal section 111a. For example, the distal section 111a may have two protrusions 111g, and the fixture 150 may have two recesses 151. The protrusions 111g may be disposed on two corresponding inside of the distal section 111a, and the recesses 151 may be formed on two corresponding outside of the fixture 150. The protrusions 111g and the recesses 151 may be corresponding with each other. When the fixture 150 may be disposed in the distal section 111a, the protrusions 111g are disposed and posited in the recesses 151 to make the fixture 150 fix to the distal section 111a. The fixture 150, the end of the distal section 111a and the camera may be glued with each other tightly in accordance with glue to avoid the camera or the fixture 150 being detached from the distal section 111a to increase the safety of patients, to reduce the risk of complications. The glue may be a waterproof clear adhesive for achieving the waterproof effect. But the present invention is not limited to the embodiments explained above. The fixture 150 is made of a plastic material. The fixture 150 may be a clear plastic.

The endoscope 100 further includes a main system (not shown), an end of a second wire of the cable 130 electronically connects to the second circuit board of the handle 120 and the other end of the second wire of the cable 130 electronically connects to the main system. The images captured from the camera 141 may be delivered from the first wire 144, the first circuit board 143, the second circuit board and the second wire to the main system to be displayed.

According to the distal section 111a, the bending section 111b and the extend section 111c of the catheter 111 of the insert tube 110 integrally formed through a metal material disclosed in the above embodiments of the invention. When the insert tube 110 may be operated with the handle 120, the bending section 111b may be elastic and bent at any angle as needed in accordance with the arrangement relationship of the first line grooves G1 and the second line grooves G2, the shape of the first line grooves G1 and the shape of the second line grooves G2 for increasing the curvature and the extensibility of the bending section 111b. Also, the catheter 111 is integrally formed through a metal material to increase the waterproof effect.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscope, comprising an insert tube and a handle, wherein the insert tube comprises:
   a catheter comprising a distal section, a bending section and an extend section integrally and seamlessly formed in one piece through a metal material;
   a plurality of first line grooves and a plurality of second line grooves formed and arranged in staggered relation on two corresponding sides of the bending section along a central axis direction of the catheter, respectively,
   wherein at least one second line groove is arranged between the first line grooves, and the first line groove and the second line groove have a first arc length and a second arc length, respectively, with a length of the first arc length being greater than a length of the second arc length;
   wherein the handle has an end connected to an end of the extend section; and
   wherein the two second line grooves are arranged between the two first line grooves to form a first shaped structure, and a number of the first shaped structures are arranged on the bending section in decreasing order to increasing order along the central axis of the catheter.

2. The endoscope according to claim 1, wherein at least two second line grooves are arranged between the two first line grooves.

3. The endoscope according to claim 1, wherein a number of the first line grooves are formed and arranged in increasing order to decreasing order to increasing order on the bending section along the central axis of the catheter.

4. The endoscope according to claim 1, wherein a first distance is between every two first line grooves.

5. The endoscope according to claim 1, wherein a plurality of different distances are between the first line grooves, respectively.

6. The endoscope according to claim 1, wherein the insert tube further comprises a controlling unit, the catheter comprises a controlling channel, the controlling unit is disposed through the controlling channel of the catheter, and an end of the controlling unit connects between the distal section and the bending section, the controlling unit controls the bending section to bend and move in accordance with the first line grooves and the second line grooves.

7. The endoscope according to claim 1, wherein the extend section comprises a third line groove, and the third line groove is formed in a spiral shape around the axis relative to the extend section.

8. The endoscope according to claim 1, wherein the insert tube further comprises a first cladding unit and a second cladding unit, the first cladding unit covers from the outer surface of the bending section to the outer surface of the extend section of the catheter, and the second cladding unit covers the first cladding unit.

9. The endoscope according to claim 1, wherein the distal section has a first diameter and the bending section has a second diameter, a length of the first diameter is greater than the length of the second diameter.

10. The endoscope according to claim 1, further comprising
    a camera module disposed in the distal end of the catheter.

11. The endoscope according to claim 1, wherein the bending section and the extend section are integrally formed without a connecting element therebetween.

12. The endoscope according to claim 1, wherein the handle is integrally attached to the extend section.

* * * * *